United States Patent [19]

De Jager et al.

[11] 4,025,546

[45] May 24, 1977

[54] PROSTAGLANDIN ANALOGUES

[75] Inventors: Evert De Jager, Oss, Netherlands; William Robert Pilgrim, Witry-les Reims, France

[73] Assignee: Akzo N.V., Arnhem, Netherlands

[22] Filed: Nov. 6, 1975

[21] Appl. No.: 629,435

[30] Foreign Application Priority Data

Nov. 11, 1974 Netherlands .................. 7414650

[52] U.S. Cl. .................. 260/473 A; 260/470; 260/516; 260/520 B; 260/559 T; 260/559 R; 424/308

[51] Int. Cl.$^2$ ...................... C07C 69/76

[58] Field of Search ........... 260/473 A, 520 B, 470, 260/516, 559 T, 559 R

[56] References Cited

UNITED STATES PATENTS 3,862,979   1/1975   Gandolfi et al. .............. 260/514 D Primary Examiner—Paul J. Killos
Attorney, Agent, or Firm—Hugo E. Weisberger

[57] ABSTRACT

The invention relates to novel prostaglandin analogues, characterized by the general formula:

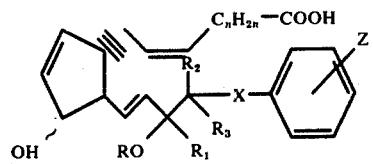

or a racemic mixture thereof, as well as esters, amides, salts and acyl derivatives of these compounds, in which $C_nH_{2n}$ represent an alkylene (2–5 C) group, R, $R_1$, $R_2$, $R_3$ represent hydrogen or alkyl (1–4 C),
X represents oxygen or sulphur and
Z represents F, Cl, Br or $CF_3$ and whereby the symbol ~ means the α or β configuration.

The compounds show a pronounced activity on the uterus and the ovary, owing to which they are very suited for initiating the partus or the termination of pregnancy.

3 Claims, No Drawings

PROSTAGLANDIN ANALOGUES

The invention relates to novel biologically active prostaglandin analogues, to processes for the preparation of these compounds and to pharmaceutical preparations containing these compounds as the active component.

The prostaglandin analogues of the invention are characterized by the general formula:

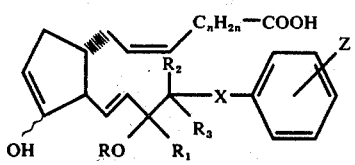

or a racemic mixture thereof, as well as esters, amides, salts and acyl derivatives of these compounds, in which $C_nH_{2n}$ represents an alkylene (2–5 C) group, R, $R_1$, $R_2$, $R_3$ represent hydrogen or alkyl (1–4 C), X represents oxygen or sulphur and Z represents F, Cl, Br or $CF_3$ and whereby the symbol ~ means the $\alpha$ or $\beta$ configuration.

The compounds of the invention have various asymmetric carbon atoms, so that various racemic and optically active diastereo-isomers are possible. These stereo-isomers are all numbered among the compounds of the invention.

The compounds I possess a pharmacological profile that substantially corresponds with that of known prostaglandins.

The present compounds are particularly characterized in that they show a much more pronounced activity on the uterus and the ovary, owing to which they are very suited for initiating the partus or the termination of pregnancy.

The present compounds are furthermore particularly suitable to be applied for the oestrus synchronisation in animals.

Compounds according to formula I which can be applied in particular, are:

11α-hydroxy-15-hydroxy-16-m.chlorophenoxy-17,18,19,20-tetranor-prosta-5,9,13-trienoic acid, 11α-hydroxy-15α-hydroxy-16-m.chlorophenoxy-17,18,19,20-tetranor-prosta-5,9,13-trienoic acid, 11α-hydroxy-15β-hydroxy-16-m.chlorophenoxy-17,18,19,20-tetranor-prosta-5,9,13-trienoic acid, 11α-hydroxy-15-hydroxy-15-methyl-16-m.chlorophenoxy-17,18,19,20-tetranor-prosta-5,9,13-trienoic acid, 11α-hydroxy-15-hydroxy-16-m.trifluoromethylphenoxy-17,18,19,20-tetranor-prosta-5,9,13-trienoic acid, 11α-hydroxy-15-hydroxy-16-p.trifluoromethylphenoxy-17,18,19,20-tetranor-prosta-5,9,13-trienoic acid, and lower aliphatic esters thereof.

The present prostaglandin analogues may be administered orally, parenterally, subcutaneously, intravaginally, intra-uterine or rectally, preferably in a daily dosage between 0.01 and 100 μ per kg body weight, dependent upon the mode of administration.

The novel prostaglandin analogues of the invention may be prepared in the manner commonly used for similar compounds. The compounds I can be prepared by the removal of one or more hydroxyl- or carboxyl-protecting groups in a compound of the general formula:

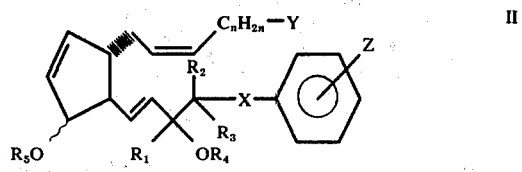

or a racemic mixture thereof, in which $C_nH_{2n}$, $R_1$, $R_2$, $R_3$, X and Z have the meaning indicated above, $R_4$ hydrogen, alkyl (1–4 C) or a hydroxyl-protecting group, $R_5$ hydrogen or a hydroxyl-protecting group and Y a carboxyl group or a protected carboxyl group, with the proviso that a protecting group is present in at least one of the groups $R_4$, $R_5$ and Y.

By a hydroxyl- or carboxyl-protecting group is meant a group that:

a. protects or chemically converts the hydroxyl or carboxyl group in such a way that this group can no longer participate in a chemical reaction and b. can be removed or converted in a convenient manner, owing to which the original hydroxyl or carboxyl group is recovered.

Effective hydroxyl protecting groups are generally obtained by esterification or etherification of the hydroxyl group in question. The esterification can be performed, for example, with aliphatic, cycloaliphatic or aromatic carboxylic- or sulphonic acids, such as, for example, formic acid, acetic acid, isobutyric acid, trichloroacetic acid, benzoic acid, p-phenylbenzoic acid, p-methylbenzoic acid, palmitic acid, oleic acid, methane sulphonic acid, ethane sulphonic acid, benzene sulphonic acid, toluene sulphonic acid, etc.

With respect to the etherification of the hydroxyl group to be protected, the latter is generally converted into an alkoxy or aralkoxy group, such as, for example methoxy, tert. butoxy, benzyloxy, p-methylbenzyloxy, phenylethoxy, diphenylmethoxy, etc. Other ether groups which can be used are a tetrahydropyranyloxy (THP) and a trimethylsilyloxy (TMS) group.

Particularly amide and ester groups are numbered among the groups that can effectively protect the carboxyl group. Preferably an esterified carboxyl group of the partial formula -COOR is used, in which R represents an organic moiety, such as, for example, a substituted or non-substituted alkyl-, cycloalkyl-, aryl- or aralkyl-group, or a silicon-containing group, preferably a trialkylsilyl group such as trimethylsilyl or dimethyl-tert.butylsilyl.

The removal of the protecting group (s) is generally carried out by means of hydrolysis or reduction in a manner which is usual in organic chemistry. The method to be followed is, however, very strongly dependent upon the nature and the chemical properties of both the relative protecting group and the protected compound in question.

For a survey of the methods which may be used in removing protecting groups, reference is made to the well-known chemical textbooks.

The compounds II, used as starting substances in the above-mentioned method, may be prepared by dehydration of a PGF type starting substance, in which both the hydroxyl group in 11-position and 15-position are effectively protected, with the general formula:

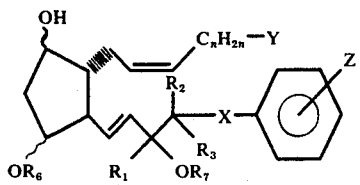

or a racemic mixture thereof, in which $C_nH_{2n}$, X, Y, Z, $R_1$, $R_2$ and $R_3$ have the meaning indicated above, $R_6$ is a hydroxyl-protecting group and $R_7$ is alkyl (1–4 C) or represent a hydroxyl protecting group.

In this dehydration the hydroxyl group in 9-position is replaced by a double bond in 9(10)-position.

The dehydration is performed in a manner usual for this kind of reaction. The dehydration may be carried out at an elevated temperature. Preferably, however, a dehydrating agent is added, such as, for example, 5,9-diazobicyclo(4,3,0)non-5-ene (DBN), a carbodiimide, or a mixture of a carbodiimide and a small amount of a copper salt. A commonly used method is the conversion of the hydroxyl group to be eliminated into an acyloxy group, for example, a tosyloxy, mesyloxy or acetoxy group followed by eliminating this acyloxy group in an acidic or alcaline medium (dependent upon the protecting groups present in the molecule) whether or not in the present of the dehydrating agent mentioned before. An alternative method is the halogenation of the hydroxyl group to be eliminated, followed by a dehydrohalogenation of the halogen group obtained, preferably under alcaline condition. In view of the smooth reaction-conditions, preference is given to the method whereby the hydroxyl group is converted into an acyloxy group. Obviously other than acyloxy groups should be used as protecting groups for the other hydroxyl groups ($R_6$ and $R_7$), for example tetrahydropyranyl or trimethylsilyl.

The compounds I can also be prepared from a compound of the general formula:

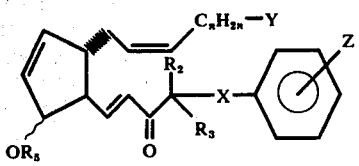

or a racemic mixture thereof, in which $C_nH_{2n}$, X, Y, Z, $R_2$, $R_3$ and $R_5$ have the meaning defined before, by reduction of the 15-keto group to the corresponding 15-OH group with, for example, metal hydrides such as zincborohydride or sodiumborohydride in a suitable solvent, for example, methanol/dimethoxyethane, or by reaction with a compound $R_8$-M, in which M represents an alkali metal or a zinc halide (ZnCl-, ZnBr-, ZnJ-, magnasium halide or cadmium halide moiety and $R_8$ is an alkyl group with 1–4 carbon atoms. This reduction of the 15-keto group generally results in a mixture of the 15α- and 15β-hydroxyl compound. A reducing agent, specifically yielding the α-hydroxyl compound, is described in J. Am. Chem. Soc. 93, 1491 (1971).

The compounds IV, used as starting substances, can be prepared by reacting a compound of the general formula V:

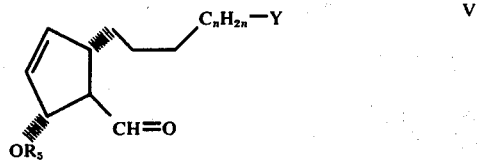

or a racemic mixture thereof, in which $C_nH_{2n}$, $R_5$ and Y have the meaning mentioned above, with a Wittig-Horner reagent of the general formula:

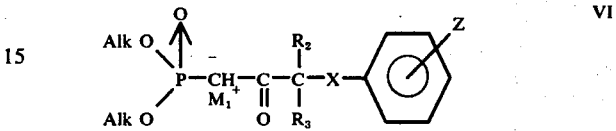

in which $R_2$, $R_3$, X and Z have the meaning mentioned before, Alk represents a lower alkyl group, and $M_1$ is an alkali metal ion.

This reagent of formula VI is obtained by treating the corresponding dialkylphosphonate of formula VI A:

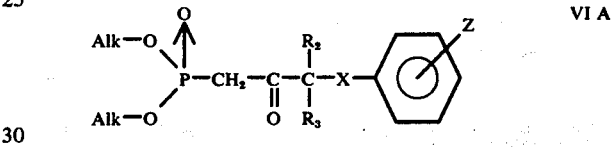

with a metal hydride, preferably sodium, potassium- or lithiumhydride or with an alkyl- or arylmetal, such as alkylsodium, alkyllithium or aryllithium.

The compounds I can further be prepared by reacting a compound of the general formula:

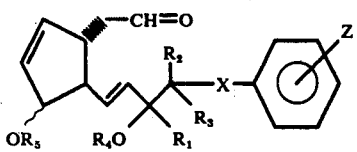

or a racemic mixture thereof, in which $R_1$, $R_2$, $R_3$, $R_4$, $R_5$, X and Z have the meaning mentioned before, with a Wittig-reagent of the general formula:

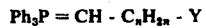

$Ph_3P = CH - C_nH_{2n} - Y$   VIII in which $C_nH_{2n}$ and Y have the meaning defined above and Ph represents an aryl or alkyl group, preferably a phenyl group. This reaction is carried out in a manner usual for Wittig reactions.

The starting substances VII can be prepared conveniently by reduction of a compound of the general formula:

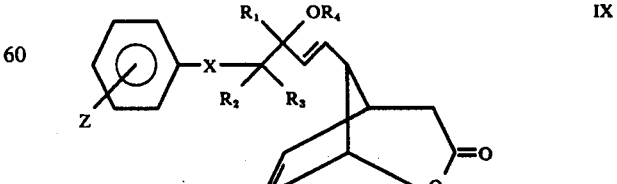

and/or the optical antipode thereof, in which $R_1$, $R_2$, $R_3$, $R_4$, X and Z have the meaning mentioned before. By this reduction the lactone of formula IX is converted through the corresponding lactol into a compound of formula VII.

Preferably di-isobutylaluminiumhydride is used for this reduction.

A method for the preparation of a compound I, in which the alicyclic hydroxy group is in β-position, starting from the corresponding α-hydroxyl compound, consists of replacing ($S_n2$ substitution) the sulphonyloxy group of a compound of the general formula:

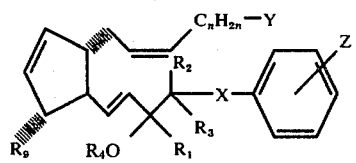

or a racemic mixture thereof, in which $R_1$, $R_2$, $R_3$, $R_4$, X, Y, Z and $C_nH_{2n}$ have the meaning indicated above and $R_9$ represents an (α)-sulphonyloxy group, such as an (α)-tosyloxy- or (α-mesyloxy group, with an acyloxy group, derived from a lower aliphatic carboxylic acid such as formic acid or acetic acid, followed by hydrolysis of the β-acyloxy group thus formed to the β-hydroxyl group.

It is obvious that mixtures of enantiomers and/or diastereo-isomers according to the general formula I which may be obtained by the reaction methods mentioned before, can, if desired, be subjected to a resolution of the racemate and/or to a separation of diastereo-isomers. They can also be converted to the functional derivatives defined above already, such as esters, amides, salts and acyl derivatives. However, it is self-evident that, for example, a methyl group (in the synthesis used for the protection of the carboxyl group) needs no longer to be eliminated, if it is planned to prepare the methylester of a compound I.

The esters, amides, salts or acyl derivatives of the present prostaglandins according to the invention may be prepared in the usual way from the corresponding compound having a free carboxyl and/or hydroxyl group.

If a Prostaglandin-acid of formula I is prepared and an alkyl ester is desired, the esterification is preferably carried out with a diazo-hydrocarbon. The methylester, for example, is obtained by reaction of the free acid I with diazo-methane. A similar use of, for example, diazo-ethane and phenyldiazomethane yields the ethyl- and benzylester respectively.

Another method for preparing esters consists of the conversion of the free acid into the corresponding silver salt, followed by reaction of the silver salt with an iodide. Examples of suitable iodides are: methyliodide, ethyliodide, butyliodide, isobutyliodide, tert. butyliodide and similar.

Amides of the present PG analogues are preferably prepared by aminolysis of the corresponding ester.

Obviously it is also possible to prepare the amides in various other manners, for example, by reaction of the acid halide or anhydride of a compound of formula I with ammonium hydroxide or a primary or secondary amine.

Pharmacologically acceptable salts of the present PG-analogues are prepared from the free acids by neutralisation with suitable inorganic or organic bases.

The free hydroxyl group(s) of the PG compounds according to formula I as well as the optional esters and amides thereof, may be acylated, if desired, preferably with an anhydride or an acid halide.

Esters of the present invention are esters derived from aliphatic alcohols with 1 to 18 carbon atoms, cycloaliphatic alcohols with 3 to 12 carbon atoms or phenyl- or phenylalkyl alcohols with 6 to 12 carbon atoms, whereby the phenyl group may be substituted with 1 to 3 halogen atoms and/or one or more alkyl groups with 1 to 4 carbon atoms of which, if desired, the terminal methyl group is substituted by 1 to 3 halogen atoms, for example, fluorine or chlorine.

Examples of aliphatic alcohols with 1 to 18 carbon atoms are: methanol, ethanol, butanol, decanol, isobutanol, tertiary butanol, pentanol, hexadecanol, octadecanol and isomers thereof. Examples of cycloaliphatic alcohols with 3 up to 12 carbon atoms, including the alkyl substituted cycloaliphatic alcohols are: cyclopropyl-, 2-methylcyclopropyl-, 2,2-dimethylcyclopropyl-, 2,3-diethylcyclopropyl-, 2-butylcyclopropyl-, cyclobutyl-, 2-metylcyclobutyl-, 3-propylcyclobutyl-, 2,3,4-triethylcyclobutyl-, cyclopentyl-, 2,2-dimethylcyclopentyl-, 3-pentylcyclopentyl-, 3-tert. butylcyclopentyl-, cyclohexyl-, 4-tert.butylcyclohexyl-, 3-isopropylcyclohexyl-, 2,2-dimethylcyclohexyl-, cycloheptyl-, cyclooctyl-, cyclononyl- and cyclodecylalcohol. Examples of phenylalkyl alcohols with 7 to 12 carbon atoms are: benzyl-, phenylethyl-, 1-phenylethyl, 2-phenylpropyl-, 4-phenylbutyl- and 3-phenylbutyl alcohol. Examples of phenols substituted by 1 to 3 halogen atoms and/or one or more alkyl groups with 1 up to 4 carbon atoms are: p-chlorophenyl-, m-chlorophenyl-, o-chlorophenyl-, 2,4-dichlorophenyl-, 2,4,6-trichlorophenyl-, p-tolyl-, m-tolyl-, o-tolyl-, p-ethylphenyl-, p-tert.butylphenyl-, 2,5-dimethylphenyl-, 4-chloro-2-methylphenyl- and 2,4-dichloro-3-methyl-phenylalcohol.

Amides which are numbered among the compounds of the present invention are both unsubstituted amides and substituted amides.

Substituted amides preferably possess one or two aliphatic groups (with 1 to 18 carbon atoms), cycloaliphatic or aromatic groups (with 5 to 18 carbon atoms), while the nitrogen atom of the amide group may likewise be included in a heterocyclic, preferably 5- or 6-membered ring.

Pharmacologically acceptable salts of the prostaglandins according to the present invention are those compounds having a pharmacologically acceptable metal cation, an ammonium cation, an amine cation or quaternary ammonium cation.

Acyl derivatives of the present compounds I, as well as the esters or salts thereof, are particularly derived from lower aliphatic acids with 1 to 6 carbon atoms.

Examples of these acyl groups are the acetyl-, butyryl-, valeryl-, or hexanoyl-group. Among these acyl moieties, the acetyl group is preferred.

One of the methods mentioned above for the manufacture of the prostaglandin analogues of the present invention is particularly preferred, namely the reaction of a compound of formula VII with the Wittig reagent of formula VIII. The preparation of the intermediate of formula VII is much shorter and more convenient than the preparation of other intermediates mentioned.

Preferred compounds according to the invention are compounds covered by the general formula I, in which (whether or not in combination):

$C_nH_{2n}$ represents an n-propylene group,
$R_1$ represents hydrogen or methyl,
$R_2$ and $R_3$ represent hydrogen,
X represents oxygen,
Z represents a chloro or trifluoromethyl group, especially in meta-position, the alicyclic hydroxyl group is in α-position, and R represents hydrogen or methyl, as well as lower aliphatic esters (1–4 C) or pharmaceutically acceptable salts thereof.

More in particular the meta-chloro compound of formula I, in which $C_{nH2n}$ is n-propylene, $R_1$, $R_2$, $R_3$ and R are hydrogen, X is oxygen and the alicyclic hydroxyl group is in α-position, as well as a lower aliphatic ester or salt thereof, are preferred.

EXAMPLE I

Preparation of
11α,15-dihydroxy-16-p-fluorophenoxy-17,18,19,20 tetranor-prosta-5,9,13-trienoic acid.

A. 5 g of 9α-Hydroxy-11α,15-bistetrahydropyranyloxy-16-p-fluoro-phenoxy-17,18,19,20-tetranor-prosta-5,13-dienoic acid were dissolved in pyridine under nitrogen and the solution obtained was then cooled to 0° C. After that 2 g of methanesulphonylchloride were added dropwise. After stirring for 4 hours at 0° C, 30 ml of water were added, after which the pyridine was distilled off for the greater part. The thus obtained residue was poured out into water. After acidification to pH 4 with the aid of a 2N oxalic acid solution the aqueous residue was extracted with ether. The combined ether layers were washed with water, dried on magnesium sulphate and evaporated. Yield: 5.5 g (oil; 96%). $R_f$ (ether): 0.20 ($SiO_2$).

B. 5.5 g of 9α-mexyloxy compound obtained under A was dissolved in 80 ml of dimethylsulphoxide (DMSO) under nitrogen, after which 1.9 g of potassium-t-butoxide (2 equivalents) in 40 ml of DMSO were added dropwise at room temperature. The mixture was then stirred for 3 hours after which water was added. The reaction mixture was acidified to pH 4 with oxalic acid and extracted with ether. The combined ether extracts were dried on magnesium sulphate and evaporated. An oil was obtained which was purified chromatographically on a silicagel column. Yield: 2.7 g (58%). $R_f$ (ether) = 0.45 ($SiO_2$).

C. The product obtained under B (2.7 g) was hydrolysed in a 100 ml mixture of acetic acid, water and THF (6:3:1) at 47° C for about 4 hours, whereafter the reaction mixture was extracted with ether. The combined ether layers were successively washed with a saturated solution of sodiumbicarbonate and a saturated solution of sodium chloride whereafter the ether layers were dried on magnesium sulphate.

After evaporating the solvent, 1.6 g oil was obtained. Yield: 86%. $R_f$ in ether:methanol (95:5) + 0.5 on $SiO_2$.

EXAMPLE II

Separation of
11α,15α-dihydroxy-16-p-fluorophenoxy-17,18,19,20-tetranor-prosta-5,9,13-trienoic acid and
11α,15β-dihydroxy-16-p-fluorophenoxy-17,18,19,20-tetranor-prosta-5,9,13-trienoic acid.

190 mg of the 15α- and 15β-epimer obtained in I.C. was separated by preparative chromatography on a silicagel plate with the aid of a mixture of chloroform, methanol and acetic acid (90:5:5) as eluens. $R_f$ in $CHCl_3$:$CH_3OH$:$CH_3COOH$ (90:5:5) = 0.32 ($SiO_2$) for the 15α-OH-epimer and 0.37 ($SiO_2$) for the 15β-OH-epimer. Yields: 66 mg and 76 mg resp.

EXAMPLE III

In the manner described in examples I and II are prepared:
11α,15-dihydroxy-16-m-trifluoromethylphenoxy-17,18,19,20-tetranor-prosta-5,9,13-trienoic acid;
11α,15-dihydroxy-16-m-chlorophenoxy-17,18,19,20-tetranor-prosta-5,9,13-trienoic acid;
11α,15-dihydroxy-15-methyl-16-m-chlorophenoxy-17,18,19,20-tetranor-prosta-5,9,13-trienoic acid;
11α,15-dihydroxy-15-propyl-16-p-fluorophenoxy-17,18,19,20-tetranor-prosta-5,9,13-trienoic acid;
11α,15-dihydroxy-16-m-trifluoromethylphenoxy-2,17,18,19,20-pentanor-prosta-5,9,13-trienoic acid;
11α,15-dihydroxy-15-ethyl-16-p-fluorophenoxy-2a-homo-17,18,19, 20-tetranor-prosta-5,9,13-trienoic acid;
11α-hydroxy-15-methoxy-16-m-chlorophenoxy-17,18,19,20-tetranor-prosta-5,9,13-trienoic acid;
11α,15α-dihydroxy-16-m-chlorophenoxy-17,18,19,20-tetranor-prosta-5,8,13-trienoic acid and the corresponding 15β-epimer;
11α,15α-dihydroxy-16-m-trifluoromethyl-17,18,19,20-tetranor-prosta-5,8,13-trienoic acid and the corresponding 15β-epimer.

EXAMPLE IV

Preparation of
11β,15-dihydroxy-16-p-fluorophenoxy-17,18,19, 20-tetranor-prosta-5,8,13-trienoic acid.

To a solution of 1.2 g of 11α-hydroxy-15-trimethylsilyloxy:16-p-fluorophenoxy-17,18,19,20-tetranor-prosta-5,8,13-trienoic acid in pyridine, 1 g of p-toluene sulphonylchloride in pyridine was added. The solution obtained was stirred for 6 hours at 10°–15° C, then acidified with 1N citric acid and subsequently extracted with ether. The combined ether layers were washed to neutral reaction, dried and evaporated.

The residue was treated with an equivalent amount of tetraethylammoniumformate in methanol and stirred for 2 hours at 15° C, after which a methanolic solution of sodium bicarbonate (10%) was added and stirred again for 1 hour at 15° C. Acidification of the reaction mixture with 1N citric acid, extraction with ether, washing the combined ether extracts to neutral reaction, drying the extract and evaporating ether yields an oily product which was immediately dissolved in a mixture of acetic acid, water and THF (20:10:3). This mixture was stirred for one hour at 38° C. Then the reaction mixture was extracted with ether. The combined ether extracts were washed to neutral reaction, dried and evaporated to dryness. For a further purification the thus obtained residue was chromatographed on a silicagel column. In this way 0.2 g of the 11β-epimer (oil) was obtained.

EXAMPLE V

In a manner similar to that of example IV are prepared:
11β,15-dihydroxy-16-m-trifluoromethylphenoxy-17,18,19,20-tetranor-prosta-5,9,13-trienoic acid;
11β,15-dihydroxy-16-m-chlorophenoxy-17,18,19,20-tetranor-prosta-5,9,13-trienoic acid;

11β,15α-dihydroxy-16-p-fluorophenoxy-17,18,19,20-tetranor-prosta-5,9,13-trienoic acid and the corresponding 15β-epimer;

11β,15-dihydroxy-15-methyl-16-m-chlorophenoxy-2a-homo-17,18, 19,20-tetranor-prosta-5,9,13-treinoic acid;

11β,15-dihydroxy-16-m-trifluoromethylphenoxy-2,17,18,19,20-pentanor-prosta-5,9,13-trienoic acid.

EXAMPLE VI

Preparation of 11α,15-dihydroxy-16-p-fluorophenoxy-17,18,19, 20-tetranor-prosta-5,9,13-trienoic acid ethylester.

A. 1.7 g of a 55%-suspension of sodium hydride in mineral oil was suspended in 200 ml of anhydrous THF. Then a solution of 8.8 g of dimethyl-2-oxo-3-(p-fluorophenoxy)-propylphosphate in 200 ml of anhydrous THF was added dropwise while stirring and in a dry nitrogen atmosphere. The mixture obtained was stirred for 1 hour at room temperature and then cooled down to 0° C, after which a solution of 7.0 g of 7-(2β-formyl-3α-tetrahydropyranyloxy-4-cyclopenten-1α-yl)-cis-5'-heptene-acid ethylester in 50 ml of anhydrous THF was added. The reaction mixture obtained was successively stirred for 15 minutes at 0° C, mixed with 500ml of water and extracted with ethyl acetate. The ethyl acetate extracts were washed with a saturated sodiumchloride solution, then dried on anhydrous sodium sulfate and after that evaporated. The residue was chromatographed on a silicagel column with the aid of a hexane-ethyl acetate (1:1) mixture. In this way 7.5 g of 11α-tetrahydropyranyloxy-15-oxo-16-p-fluorophenoxy:17,18, 19, 20-tetranor-prosta-5,9,13-trienoic acid ethylester were obtained as a colourless oil. Yield: $R_f$ (ether) 0.60 ($SiO_2$). B. The compound obtained under A (7.5 g) was dissolved in a 350 ml mixture of dimethoxyethane and methanol (1:1), whereafter the solution was cooled down to 0° C. Then 90 ml of a 0.14M solution of sodiumborohydride in anhydrous dimethoyethane were added dropwise at 0°–3° C while stirring. After having added this solution completely, stirring was continued for one hour at 0° C, whereafter the reaction mixture was diluted with 500 mil of water and extracted (3x) with ether in portions of 250 ml. The combined ether-layers were dried on anhydrous sodium sulphate and evaporated. The residue obtained was chromatographed on silicagel with the aid of ether. This provided 5.2 g of 11α-tetrahydropyranyloxy-15-hydroxy-16-p-fluorophenoxy-17,18,19,20-tetranor-prosta-5,9,13-trienoic acid ethylester as a mixture of both $C_{15}$-epimers (oil).

Yield: 69%. $R_f$ (ether) = 0.38 ($SiO_2$). C. Removal of the tetrahydropyranyl group in a manner as descrbied in example I C, yielded 3.8 g of 11α,15-dihydroxy-16-p-fluorophenyloxy-17,18,19,20-tetranor-prosta-5,9,13-trienoic acid ethylester. Yield: 91%. $R_f$ (ether) = 0.25 ($SiO_2$).

EXAMPLE VII

In a manner similar to that of example VI are prepared: 11α, 15-dihydroxy-16-m-trifluoromethylphenoxy-17,18,19,20-tetranor-prosta-5,9,13-trienoic acid ethylester: 11α,15-dihydroxy-16m-chlorophenoxy.17,18,19,20-tetranor-prosta-5,9,13-trienoic acid ethylester.

EXAMPLE VIII

Preparation of 11α,15-dihydroxy-15-methyl-16-p-fluorophenoxy-17,18,19,20-tetranor-prosta-5,9,13-trienoic acid ethylester. A. 7.5 g of 11α-tetrahydropyranyloxy-15-oxo-16-p-fluorophenoxy-17,18,19,20-tetranor-prosta-5,9,13-trienoic acid ethylester were dissolved in 250ml of anhydrous ether. The solution obtained was cooled down to −40° C in a nitrogen atmosphere, whereafter, while stirring at −40° C, 40 ml of an 0.38M solution of metylmagnesium iodide in anhydrous ether were added dropwise in about 30 minutes. Stirring at −40° C was continued for 1 hour. Then an aqueous solution of ammonium chloride was added to the reaction mixture, while stirring. After separation of the organic layer, the aqueous layer was extracted with 100 ml of ether. The combined organic layers were dried on anhydrous sodium sulphate and then evaporated. Chromatographic purification of the residue on silicagel with the acid of ether afforded 4.4 g of 11α-tetrahydropyranyloxy-15-hydroxy-15-methyl-16p-fluorophenoxy-17,18,19,20-tetranor-prosta-5,9,13-trienoic acid ethylester as a colourless oil. Yield: 57% ($R_f$ (ether) = 0.40 ($SiO_2$). B. Removal of the tetrahydropyranyl group in the manner as described in example I C yielded the free 11α-hydroxycompound as a mixture of the 15α- and 15β-hydroxy-epimers.

EXAMPLE IX

In a manner similar to that of example VIII are prepared:
11α, 15-dihydroxy-15-methyl-16-m-chlorophenoxy-17,18,19,20-tetranor-prosta-5,9,13-trienoic acid ethylester ;
11α,15-dihydroxy-15-ethyl-16-m-chlorophenoxy-17,18,19,20-tetranor-prosta-5,9,13-trienoic acid ethylester;
11α,15-dihydroxy-15-methyl-16-m-trifluoromethylphenoxy-17,18,19,20-tetranor-prosta-5,9,13-trienoic acid benzylester.

EXAMPLE X

Preparation of 11α,15 (α and β)-dihydroxy-16-p-fluorophenoxy-17,18,19,20-tetranor-prosta-5,9,13-trienoic acid.

A. To a solution of 10.6 g of 5-triphenylphosphoniovaleric acid bromide in 40 ml of andyrous DMSO was added dropwise and in nitrogen atmosphere, 32 ml of an 1.5M solution of dimsyl-sodium in DMSO. The solution obtained was cooled in ice, whereafter a solution of 1.22 g of 2 β-(3'-hydroxy-4'-p-flurorphenoxy-trans-1'-butenyl)-3α-hydroxy-4-cyclopenten-1α-ethanal in 3 ml of dry DMSO was added quickly. After stirring for 5 minutes, 100 ml of water were added under cooling with ice. The mixture obtained was acidified to pH 5 with the aid of 2N $H_2SO_4$ and subsequently extracted three times with ether in portions of 100 ml. The combined ether extracts were washed with water (1x), dried on anhydrous sodium sulphate and then evaporated.

B. The mixture of epimers obtained under A was separated and the 15α-hydroxy epimer and the 15β-hydroxy epimer were isolated in the usual way (reference is made to example II). Yield: 15α-hydroxy epimer: 0.52g; $R_f$ (ether): 0.20 ($SiO_2$): Yield 15β-hydroxy epimer: 0.46 g; $R_f$ (ether): 0.30 ($SiO_2$). Total yield: 63%.

C. Starting from 2β-(3'α-hydroxy-4'-p-fluorophenoxytrans-1'-butenyl)-3α-hydroxy-4-cyclopenten:-1α-yl-ethanal and 5-triphenylphosphoniovaleric acid bromide, the 11α, 15α-dihydroxy-16-p-fluorophenoxy-17,18,19,20-tetranor-prosta-5,9,13-trienoic acid was directly obtained in the way described in A.

EXAMPLE XI

In a manner similar to that of example X are prepared:

11α15-dihydroxy-16-m-chlorophenoxy-17,18,19,20-tetranorprosta-5,9,13-trienoic acid;

11α-dihydroxy-16-m-chlorophenoxy-17,18,19,20-tetranorprosta-5,9,13-trienoic acid;

11α,15β-dihydroxy-16-m-chlorophenoxy-17,18,19,20-tetranorprosta-5,9,13-trienoic acid;

11α15-dihydroxy-15-methyl-16-m-chlorophenoxy-17,18,19,20-tetranor-prosta-5,9,13-trienoic acid;

11α,15-dihydroxy-15 -methyl-16-m-trifluoromethylphenoxy-17,18,19,20-tetranor-prosta-5,9,13-trienoic acid ethyl-ester;

11α,15-dihydroxy-16-m-chlorothiophenoxy-17,18,19,20-tetranorprosta-5,9,13-trienoic acid;

11α-hydroxy-15-methoxy-16-m-chlorophenoxy-17,18,19,20-tetranor-prosta-5,9,13-trienoic acid (both 15-epimers)

EXAMPLE XII

11α,15-dihydroxy-16-p-fluorophenoxy-17,18,19,20-tetranorprosta-5,9,13-trienoic acid methylester.

0.25 g 11α,15-Dihydroxy-16-p-fluorophenoxy-17,18,19,20-tetranor-prosta-5,9,13-trienoic acid was dissolved in 10 ml anhydrous ether. The solution was cooled in ice and a solution of diazomethane in ether (ca. 0.2M) was added dropwise until the mixture acquired a permanent pale yellow colour. After evaporation of the solvent the crude ester was chromatographed over silicagel with ether. The product was obtained as an oil (0.15 g) $R_f$ (ether): 0.18 ($SiO_2$).

We claim:

1. A prostaglandin analogue of the general formula:

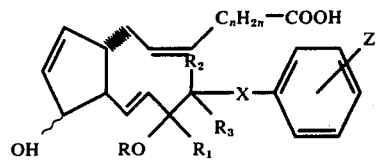

or a racemate thereof, and pharmaceutically acceptable salts, esters, amides and acyl derivatives thereof, in which $C_nH_{2n}$ represents alkylene (2–5 C), R, $R_1$, $R_2$, $R_3$ represent hydrogen or alkyl (1–4 C), X represents oxygen or sulphur, Z represents F, Cl, Br or $CF_3$, and the symbol ≀ indicates the α-or β-configuration.

2. A prostaglandin analoque according to claim 1 of the formula:

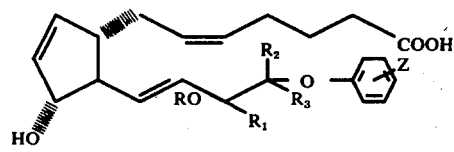

or a racemate thereof, in which $R_1$, $R_2$, $R_3$ and Z have the meanings indicated in claim 1 as well as lower aliphatic esters or pharamaceutically acceptable salts thereof.

3. A compound according to claim 2 of the formula:

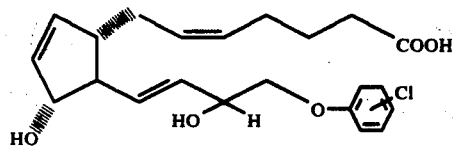

or racemate thereof, and lower aliphatic esters of salts of these compounds.

* * * * *